(12) United States Patent
Davis et al.

(10) Patent No.: US 12,421,478 B2
(45) Date of Patent: Sep. 23, 2025

(54) STABILIZATION OF HYDROGEN PEROXIDE CONTAINING FORMULATIONS WITH TWO-COMPONENT SYNERGISTIC STABILIZERS

(71) Applicants: John P. Davis, Danville, IL (US); Joshua K. Clemence, Bozeman, MT (US); Noah Durham, Champaign, IL (US); Kayla Marrow, Danville, IL (US)

(72) Inventors: John P. Davis, Danville, IL (US); Joshua K. Clemence, Bozeman, MT (US); Noah Durham, Champaign, IL (US); Kayla Marrow, Danville, IL (US)

(73) Assignee: EnvirOx, L.L.C., Danville, IL (US)

( * ) Notice: Subject to any disclaimer, the term of this patent is extended or adjusted under 35 U.S.C. 154(b) by 302 days.

(21) Appl. No.: 18/223,203

(22) Filed: Jul. 18, 2023

(65) Prior Publication Data
US 2024/0043775 A1    Feb. 8, 2024

Related U.S. Application Data

(60) Provisional application No. 63/392,901, filed on Jul. 28, 2022.

(51) Int. Cl.
| | | |
|---|---|---|
| C11D 3/00 | (2006.01) | |
| C07C 69/732 | (2006.01) | |
| C07C 69/88 | (2006.01) | |
| C11D 3/20 | (2006.01) | |
| C11D 3/39 | (2006.01) | |
| C11D 3/40 | (2006.01) | |
| C11D 3/50 | (2006.01) | |

(52) U.S. Cl.
CPC ............ *C11D 3/394* (2013.01); *C07C 69/732* (2013.01); *C07C 69/88* (2013.01); *C11D 3/0084* (2013.01); *C11D 3/2093* (2013.01); *C11D 3/40* (2013.01); *C11D 3/50* (2013.01)

(58) Field of Classification Search
CPC ..... C11D 3/394; C11D 3/0084; C11D 3/2093; C11D 3/40; C11D 3/50; C11D 3/3947; C07C 69/732; C07C 69/88
USPC .......................................................... 510/372
See application file for complete search history.

(56) References Cited

U.S. PATENT DOCUMENTS

| | | |
|---|---|---|
| 2,371,545 A | 3/1945 | Riggs et al. |
| 2,886,532 A | 5/1959 | Richmond et al. |

(Continued)

FOREIGN PATENT DOCUMENTS

| | | |
|---|---|---|
| JP | 2016/120276 | 7/2016 |
| WO | WO 2000/063337 | 10/2000 |

(Continued)

OTHER PUBLICATIONS

STIC Search Report dated Jul. 15, 2025.*

(Continued)

*Primary Examiner* — Eisa B Elhilo
(74) *Attorney, Agent, or Firm* — King & Partners, PLC (57) ABSTRACT

A cleaning solution, including: a solvent; an oxidizing agent, wherein the oxidizing agent comprises a peroxide; a stabilizing system, wherein the stabilizing system comprises a first stabilizing agent and a second stabilizing agent; a surfactant; an optional colorant; and an optional fragrance.

16 Claims, 4 Drawing Sheets

(56) References Cited

U.S. PATENT DOCUMENTS

| | | |
|---|---|---|
| 3,635,828 A | 1/1972 | Benjamin et al. |
| 3,869,401 A | 3/1975 | Ernst |
| 3,977,826 A | 8/1976 | Iscowitz |
| 4,022,703 A | 5/1977 | Bakes et al. |
| 4,130,501 A | 12/1978 | Lutz et al. |
| 4,146,499 A | 3/1979 | Rosano |
| 4,230,478 A | 10/1980 | Zumbrunn |
| 4,362,706 A | 12/1982 | Willard |
| 4,414,128 A | 11/1983 | Goffinet |
| 4,430,236 A | 2/1984 | Franks |
| 4,472,291 A | 9/1984 | Rosano |
| 4,530,781 A | 7/1985 | Gipp |
| 4,656,043 A | 4/1987 | Hawkins et al. |
| 4,704,225 A | 11/1987 | Stoufer |
| 4,711,739 A | 12/1987 | Kandathil |
| 4,749,516 A | 6/1988 | Brusky |
| 4,829,897 A | 5/1989 | Wyman |
| 4,877,544 A | 10/1989 | Gabriel et al. |
| 4,900,468 A | 2/1990 | Mitchell et al. |
| 5,008,030 A | 4/1991 | Cook |
| 5,076,954 A | 12/1991 | Loth et al. |
| 5,102,575 A | 4/1992 | Lanniel et al. |
| 5,130,124 A | 7/1992 | Merianos et al. |
| 5,180,514 A | 1/1993 | Farr et al. |
| 5,213,624 A | 5/1993 | Williams |
| 5,281,280 A | 1/1994 | Lisowski |
| 5,281,354 A | 1/1994 | Faber |
| 5,320,805 A | 6/1994 | Kramer et al. |
| 5,336,426 A | 8/1994 | Rader et al. |
| 5,368,867 A | 11/1994 | DaSilva |
| 5,376,297 A | 12/1994 | Choy |
| 5,380,457 A | 1/1995 | Zielske |
| 5,389,157 A | 2/1995 | Smith |
| 5,399,282 A | 3/1995 | Hansen |
| 5,527,486 A | 6/1996 | De Guertechin |
| 5,531,938 A | 7/1996 | Erilli |
| 5,549,840 A | 8/1996 | Mondin et al. |
| 5,585,034 A | 12/1996 | Lysy et al. |
| 5,602,090 A | 2/1997 | Melikyan et al. |
| 5,614,484 A | 3/1997 | Panadiker |
| 5,653,970 A | 8/1997 | Vermeer |
| 5,696,171 A | 12/1997 | Rupp et al. |
| 6,316,399 B1 | 11/2001 | Melikyan et al. |
| 6,462,010 B1 | 10/2002 | Aszman et al. |
| 6,696,399 B1 | 2/2004 | Chernin et al. |
| 6,753,306 B2 | 6/2004 | Simpson |
| 6,939,839 B2 | 9/2005 | Johnson |
| 7,148,187 B1 | 12/2006 | Simon et al. |
| 7,439,218 B2 | 10/2008 | Bowker |
| 7,879,787 B2 | 2/2011 | Heintz et al. |
| 8,375,494 B2 | 2/2013 | Hammock |
| 8,618,038 B1 | 12/2013 | Hunt et al. |
| 10,119,099 B2 | 11/2018 | Clemence et al. |
| 11,026,418 B2 | 6/2021 | Lan et al. |
| 11,518,966 B2 | 12/2022 | Stewart et al. |
| 2009/0061718 A1 | 3/2009 | Seidling et al. |
| 2012/0230925 A1* | 9/2012 | Wagner ............... A61K 8/4973 510/214 |
| 2014/0135297 A1 | 5/2014 | Narayanan et al. |
| 2015/0126759 A1* | 5/2015 | Boaz .................... A61Q 19/08 554/138 |
| 2015/0361381 A1* | 12/2015 | Ebert .................... C11D 1/662 510/218 |
| 2018/0371370 A1 | 12/2018 | Keuleers et al. |
| 2019/0208774 A1* | 7/2019 | Lei ........................ C02F 1/50 |
| 2020/0032167 A1* | 1/2020 | Qin ...................... C08K 5/0041 |
| 2022/0002636 A1 | 1/2022 | Man et al. |
| 2022/0015359 A1 | 1/2022 | Ortmann |

FOREIGN PATENT DOCUMENTS

| | | | |
|---|---|---|---|
| WO | WO 2011042423 A2 * | 4/2011 | ............... A61Q 5/06 |
| WO | WO 2014081950 A2 * | 5/2014 | ........... C11D 3/3707 |
| WO | WO 2014/131584 | 9/2014 | |

OTHER PUBLICATIONS

PCT Written Opinion of the International Searching Authority for International Application No. PCT/US23/028007 mailed Oct. 31, 2023.

* cited by examiner

STABILIZATION OF HYDROGEN PEROXIDE CONTAINING FORMULATIONS WITH TWO-COMPONENT SYNERGISTIC STABILIZERS

CROSS-REFERENCE TO RELATED APPLICATIONS

This application claims the benefit of U.S. Provisional Application Ser. No. 63/392,901, entitled "STABILIZATION OF HYDROGEN PEROXIDE CONTAINING FORMULATIONS WITH TWO-COMPONENT SYNERGISTIC STABILIZERS," filed Jul. 28, 2022—which is hereby incorporated herein by reference in its entirety, including all references cited therein.

STATEMENT REGARDING FEDERALLY SPONSORED RESEARCH OR DEVELOPMENT

Not applicable.

REFERENCE TO A SEQUENCE LISTING

Not applicable.

BACKGROUND OF THE INVENTION

1. Field of the Invention

The present invention relates in general to formulations (e.g., multi-purpose cleaning, bleaching, degreasing, sanitizing, and/or disinfecting formulations), and, more particularly, to novel, peroxide-based formulations that are stabilized using a two-component stabilizer system. This system concurrently stabilizes other components within the formulations, including, but not limited to, active ingredients, inactive ingredients, such as colorants, fragrances, adjunct agents, etcetera.

2. Background Art

Cleaning solutions and associated formulations have been known in the art for years and are the subject of a plurality of patents and/or publications, including: U.S. Pat. No. 8,375,494 entitled "Cleaning Compositions Containing A Corrosion Inhibitor," U.S. Pat. No. 7,879,787 entitled "Cleaning Compositions For Hard To Remove Organic Material," U.S. Pat. No. 7,439,218 entitled "Disinfectant Compositions Comprising An Orange Oil Mixture And Methods Of Use Thereof," U.S. Pat. No. 6,939,839 entitled "Cleaning Composition With Terpene And Hydrogen Peroxide," U.S. Pat. No. 5,653,970 entitled "Personal Product Compositions Comprising Heteroatom Containing Alkyl Aldonamide Compounds," U.S. Pat. No. 5,602,090 entitled "Surfactant Based Aqueous Compositions With D-Limonene And Hydrogen Peroxide And Methods Using The Same," U.S. Pat. No. 5,549,840 entitled "Cleaning Composition In Microemulsion, Liquid Crystal Or Aqueous Solution Form Comprising Mixture Of Partially Esterified, Full Esterified And Non-Esterified Ethoxylated Polyhydric Alcohols," U.S. Pat. No. 5,281,354 entitled "Liquid Cleanser Composition," U.S. Pat. No. 4,877,544 entitled "Oxidation Stable Surfactants," and U.S. Pat. No. 4,472,291 entitled "High Viscosity Microemulsions" all of which are hereby incorporated herein by reference in their entirety—including all references cited therein.

U.S. Pat. No. 8,375,494 appears to disclose cleaning compositions containing a corrosion inhibitor for removing soil from carpets, upholstery and the like without subjecting common metal alloys used in aircraft and other constructions to corrosive attack. The cleaning compositions include at least one dispersing agent, at least one anti-redeposition agent, at least one corrosion inhibitor, at least one pH modifier, at least one chelating agent and at least one stabilizing agent. The compositions also optionally include at least one fragrance and/or at least one preservative agent.

U.S. Pat. No. 7,879,787 appears to disclose an oxidizing cleaning composition that comprises a low concentration of aqueous hydrogen peroxide that is environmentally friendly and has stability in strong alkaline solutions. The aqueous hydrogen peroxide composition contains a combination of one or more hydrophilic surfactants having an HLB of 10 or greater, one or more hydrotropes, one or more UV-analyzable surfactants having an aromatic detectable functional group, and optionally a surfactant having an HLB of less than 10. The cleaning composition when mixed with an alkaline compound purports to be very effective in removing dried or baked residues of polymers, modified or natural celluloses starches, natural gels, and the like at low concentrations and temperatures.

U.S. Pat. No. 7,439,218 appears to disclose a disinfectant composition comprising hydrogen peroxide ($H_2O_2$), orange terpene oil, orange valencia oil, a non-ionic emulsifier, and distilled or deionized water ($H_2O$).

U.S. Pat. No. 6,939,839 appears to disclose a cleaning composition that uses a terpene such as D-limonene or orange oil, a nonionic surfactant, a single anionic surfactant, an anti-oxidant, hydrogen peroxide, and the balance deionized water.

U.S. Pat. No. 5,653,970 appears to disclose personal product compositions having heteroatom containing alkyl aldonamide compounds and a skin-conditioning agent. The '970 patent teaches that when these heteroatom containing alkyl aldonamides are used, benefits such as enhanced stability and/or enhanced viscosity are obtained relative to the use of other known thickeners or non-heteroatom containing aldonamides.

U.S. Pat. No. 5,602,090 appears to disclose a cleaning composition including a terpene such as D-limonene and hydrogen peroxide in a surfactant based aqueous solution. The composition in various specific formulations is a microemulsion useful for a variety of materials for both industrial and household applications.

U.S. Pat. No. 5,549,840 appears to disclose liquid crystal compositions or microemulsion compositions that are effective in the removal of oily and greasy soil and have evidenced grease release effect. Such compositions contain an anionic detergent, an ethoxylated glycerol type compound, a hydrocarbon ingredient, and water which comprises the use of a water-insoluble odoriferous perfume as the essential hydrocarbon ingredient in a proportion sufficient to form a dilute o/w microemulsion composition.

U.S. Pat. No. 5,281,354 appears to disclose a liquid cleanser composition, particularly for use as a hard surface cleanser that comprises a mixture of from about 0.5% to about 10% of a terpene selected from mono- and sesquiterpenes and mixtures thereof, from about 1% to about 10% of a water miscible solvent, and, from about 1% to about 10% of an amide surfactant. The '354 patent also discloses that the composition can contain from about 10% to about 70% of a water-insoluble abrasive.

U.S. Pat. No. 4,877,544 appears to disclose detergent compositions comprising a special type of oxidation resistant nonionic surfactant and an oxidizing agent which may either be a hypochlorite or a peroxygen material. The surfactant component structurally comprises a $C_8$-$C_{12}$ alkyl substituted phenoxy hydrophobe alkoxylated with ethylene oxide and/or propylene oxide, with the proviso that the ratio of ethylene oxide to propylene oxide is at least 1 but no higher than 10. Methyl or chloroethyl groups are used to endcap the surfactant.

U.S. Pat. No. 4,472,291 appears to disclose an oil-in-water microemulsion of increased viscosity. The microemulsion comprises an aqueous continuous phase, an oil phase, a primary surfactant having a lipophilic moiety and a hydrophilic moiety, wherein the hydrophilic moiety carries an electrostatic charge and a cosurfactant. The viscosity is increased by adding a secondary surfactant which is characterized by a long chain lipophilic moiety and a charged hydrophilic moiety which is reactive with the charged hydrophilic moiety of the primary surfactant. In forming the microemulsion of increased viscosity, the microemulsion is formed first in the absence of the secondary surfactant, and the secondary surfactant is added thereto.

While the cleaning solutions and formulations disclosed supra have been known in the art for years, issues associated with formulation performance, color, odor, and extended shelf life while maintaining environmentally preferred characteristics remain largely problematic and/or unsolved. As such, there is a genuine demand for novel peroxide-based formulations that are stabilized using a two-component stabilizer system.

These and other objects of the present invention will become apparent in light of the present specification, claims, chemical structures, chemical formulae, and drawings.

SUMMARY OF THE INVENTION

The present invention is directed to a cleaning solution comprising, consisting essentially of, and/or consisting of: (1) a solvent; (2) an oxidizing agent, wherein the oxidizing agent comprises a peroxide; (3) a stabilizing system, wherein the stabilizing system comprises: (a) a first stabilizing agent, and (b) a second stabilizing agent; (4) a surfactant; (5) an optional colorant; and (6) an optional fragrance.

In a preferred embodiment of the present invention, the solvent comprises water.

In another preferred embodiment of the present invention, the peroxide is selected from the group consisting of an inorganic peroxide and/or an organic peroxide.

In yet another preferred embodiment of the present invention, the peroxide comprises hydrogen peroxide.

In a preferred implementation of the present invention, the first stabilizing agent comprises a sterically hindered phenolic antioxidant, and the second stabilizing agent comprises an organic ester.

In another preferred implementation of the present invention, the first stabilizing agent is a compound represented by the structure of formula (I):

wherein $R_1$-$R_3$ are each independently selected from the group consisting of H, OH, and an alkyl, aryl, alkoxy, alkanoyl, aroyl, alkenyl, and/or cyano group containing 1 to approximately 25 carbon atom(s) with the proviso that at least one of $R_1$-$R_3$ is OH; wherein m ranges from 1 to approximately 20; and wherein n ranges from 1 to approximately 20. It will be understood, that unless specified otherwise, the term approximately, as used herein, will be defined as the value, number, and/or integer+/−10 percent.

In yet another preferred implementation of the present invention, the first stabilizing agent is a compound represented by the structure of formula (II):

wherein $R_1$-$R_3$ are each independently selected from the group consisting of H, OH, and an alkyl, aryl, alkoxy, alkanoyl, aroyl, alkenyl, and/or cyano group containing 1 to approximately 25 carbon atom(s) with the proviso that at least one of $R_1$-$R_3$ is OH; and wherein m ranges from 1 to approximately 5.

In one aspect of the present invention, the first stabilizing agent is a compound represented by the structure of formula (III):

In a preferred embodiment of the present invention, the second stabilizing agent is a compound represented by the structure of formula (IV):

wherein $R_1$-$R_3$ are each independently selected from the group consisting of H, OH, and an alkyl, aryl, alkoxy, alkanoyl, aroyl, alkenyl, and/or cyano group containing 1 to approximately 25 carbon atom(s) with the proviso that at least one of $R_1$-$R_3$ is OH; and wherein m ranges from 1 to approximately 20.

In another preferred embodiment of the present invention, the second stabilizing agent is a compound represented by the structure of formula (V):

(V)

wherein m ranges from 1 to approximately 20.

In yet another preferred embodiment of the present invention, the second stabilizing agent is a compound represented by the structure of formula (VI):

(VI)

In one preferred embodiment of the present invention, the surfactant comprises a non-ionic surfactant, an anionic surfactant, a cationic surfactant, a zwitterionic surfactant, and combinations thereof.

Preferably, the optional colorant/fragrance is D-limonene, and/or orange oil.

The present invention is also directed to a cleaning solution comprising, consisting essentially of, and/or consisting of: (1) a solvent, wherein the solvent is water; (2) an oxidizing agent, wherein the oxidizing agent is hydrogen peroxide; (3) a stabilizing system, wherein the stabilizing system comprises a first stabilizing agent and a second stabilizing agent, wherein the first stabilizing agent is a sterically hindered phenolic antioxidant and the second stabilizing agent is an organic ester; (4) a surfactant, wherein the surfactant is a non-ionic surfactant, an anionic surfactant, a cationic surfactant, a zwitterionic surfactant, and combinations thereof; and (5) a colorant/fragrance, wherein the colorant/fragrance is orange oil.

The present invention is further directed to a cleaning solution comprising, consisting essentially of, and/or consisting of: a cleaning solution, consisting of: (1) from approximately 75% to approximately 98% by weight a solvent, wherein the solvent is water; (2) from approximately 0.5% to approximately 5.0% an oxidizing agent, wherein the oxidizing agent is hydrogen peroxide; (3) from approximately 0.01% to approximately 2.0% a stabilizing system, wherein the stabilizing system comprises pentaerythritol tetrakis(3-(3,5-di-tert-butyl-4-hydroxyphenyl) propionate) and octyl gallate; (4) from approximately 0.5% to approximately 15.00% a surfactant; (5) from approximately 0.5% to approximately 5.00% a colorant/fragrance; and (6) wherein any remainder comprises one or more adjunct agents.

BRIEF DESCRIPTION OF THE DRAWINGS

Certain embodiments of the present invention are illustrated by the accompanying figures. It will be understood that the figures are not necessarily to scale and that details not necessary for an understanding of the invention or that render other details difficult to perceive may be omitted.

It will be further understood that the invention is not necessarily limited to the particular embodiments illustrated herein.

The invention will now be described with reference to the drawings wherein.

DETAILED DESCRIPTION OF THE INVENTION

Figure 1:
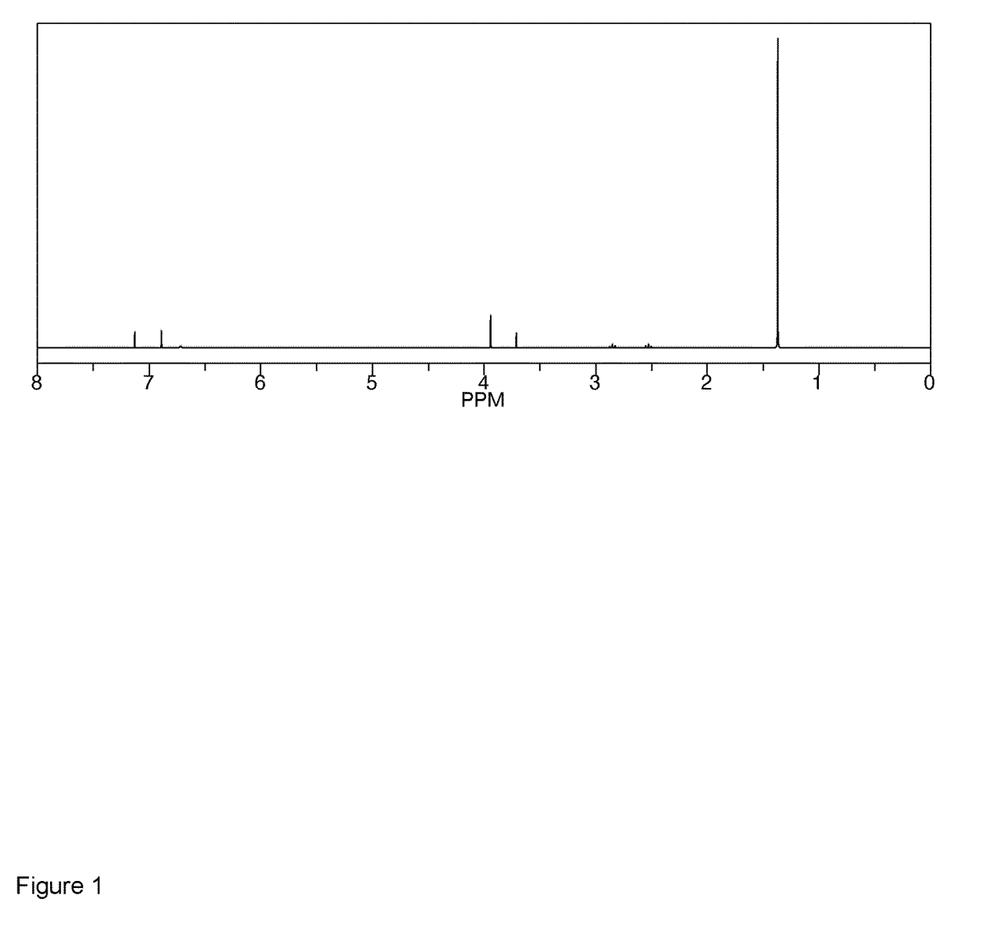
FIG. 1 of the drawings is a $^1$H-NMR spectrogram of a first stabilizing agent (pentaerythritol tetrakis(3-(3,5-di-tert-butyl-4-hydroxyphenyl)-propionate))
Figure 2:
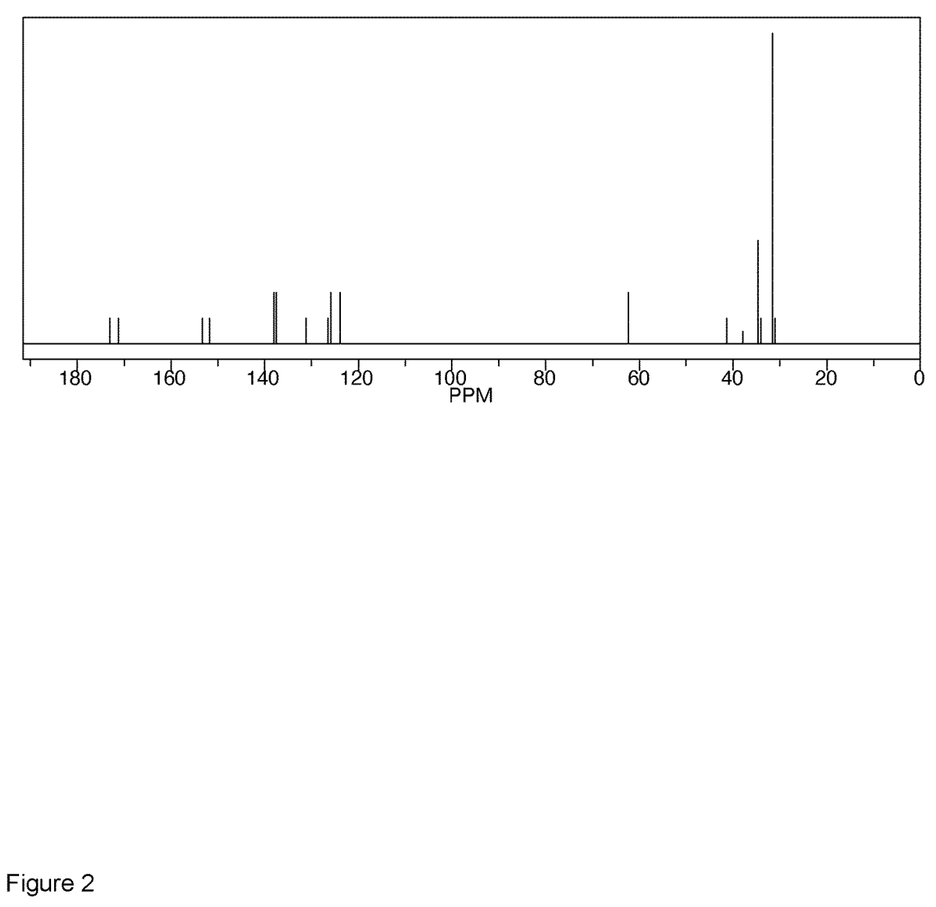
FIG. 2 of the drawings is a $^{13}$C-NMR spectrogram of a first stabilizing agent (pentaerythritol tetrakis(3-(3,5-di-tert-butyl-4-hydroxyphenyl)-propionate))
Figure 3:
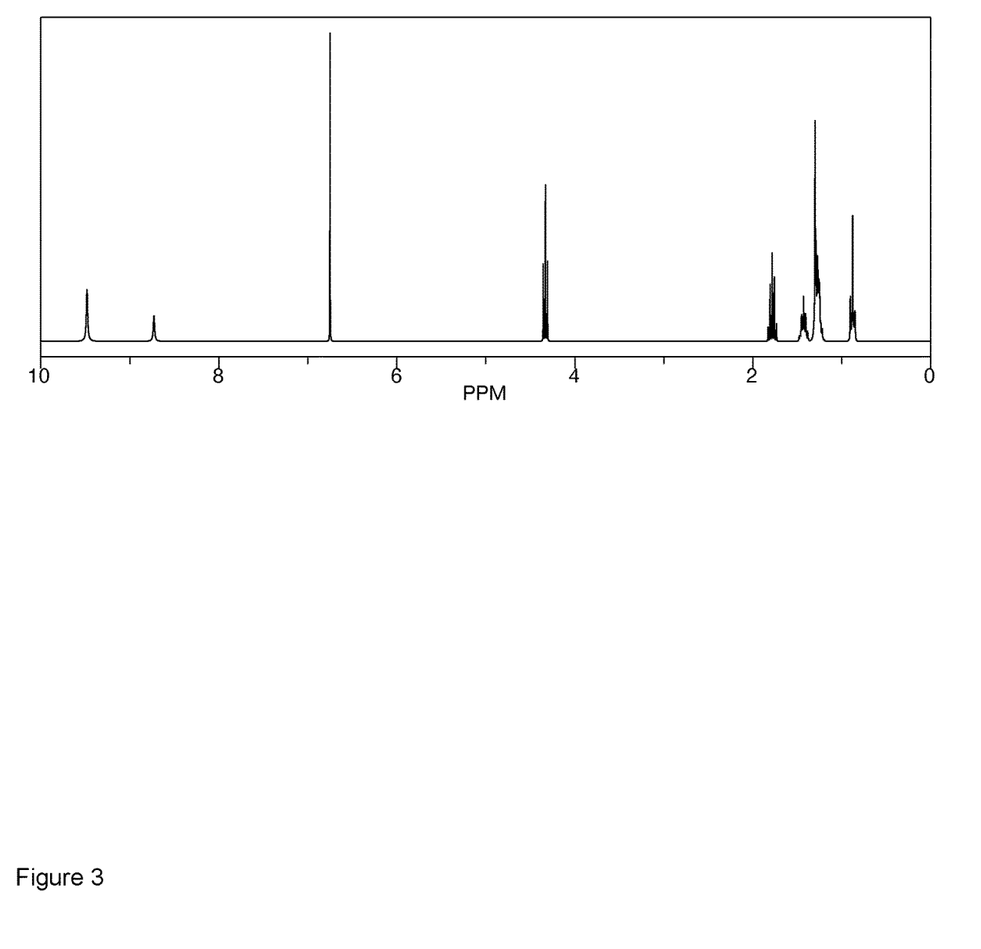
FIG. 3 of the drawings is a 1H-NMR spectrogram of a second stabilizing agent (octyl gallate)
Figure 4:
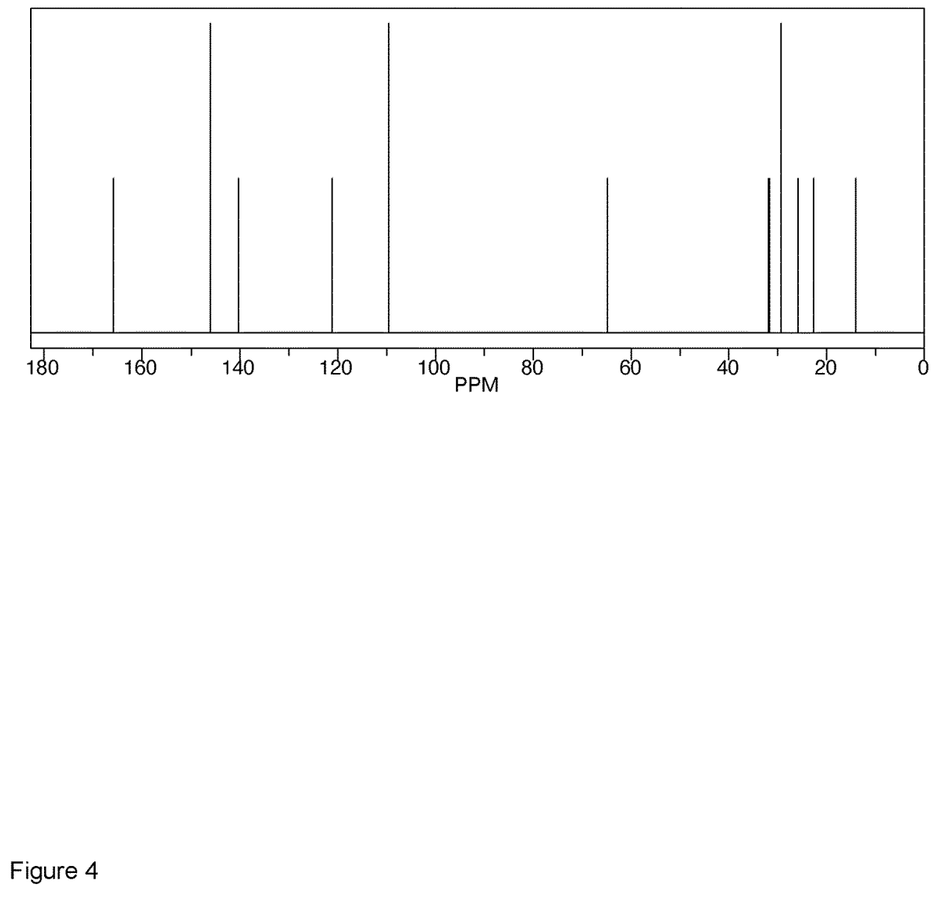
FIG. 4 of the drawings is a $^{13}$C-NMR spectrogram of a second stabilizing agent (octyl gallate).

While this invention is susceptible of embodiment in many different forms, there is shown in the structural formulas and described herein in detail several specific embodiments with the understanding that the present disclosure is to be considered as an exemplification of the principles of the invention and is not intended to limit the invention to the embodiments illustrated. It will be understood that the structural formulas disclosed herein are intended to comprise all stereochemical configurations regardless of graphical representations.

In accordance with the present invention, peroxide-based cleaning, bleaching, degreasing, sanitizing, and/or disinfecting solutions are disclosed herein that are stabilized using a two-component stabilizer system.

In one embodiment of the present invention, the cleaning solution comprises: a solvent, an oxidizing agent, a stabilizing system, a surfactant, an optional colorant, and an optional fragrance.

For purposes of the present disclosure, the solvent of the solution may comprise one or more of any one of a number of common, commercially available solvents, including polar solvents and/or non-polar solvents. Specific examples of preferred solvents include, for example, water, deionized, distilled, and/or reverse osmosis water, hexane, acetone, methyl ethyl ketone, toluene, benzene, ethers, 3-methylsulfolane, glutaronitrile, dimethyl sulfoxide, dimethyl formamide, acetonitrile, polyethers including tetraglyme, alcohols including ethoxyethanol, nitriles including 3-hydroxypropionitrile, 2-methylglutaronitrile, ketones including 2-acetylbutyrolactone, cyclopentanone, cyclic esters including beta-propiolactone, gamma-butyrolactone, gamma-valerolactone, propylene carbonate, ethylene carbonate and homogenous mixtures of the same. While specific solvents have been disclosed, for illustrative purposes only, as being suitable solvents, numerous other solvents that would be known to those having ordinary skill in the art having the present disclosure before them are likewise contemplated for use. Indeed, it will be understood that non-liquid or polymer type media are suitable for use in accordance with the present invention. Preferably, the solvent is present in a concentration ranging from approximately (i.e., +/−10 percent) 60 percent by weight to approximately (i.e., +/−10 percent) 98 percent by weight, and more preferably from approximately (i.e., +/−10 percent) 75 percent by weight to approximately (i.e., +/−10 percent) 98 percent by weight.

In one embodiment of the present invention, the oxidizing agent comprises a peroxide, such an inorganic peroxide (e.g., hydrogen peroxide, 35% aqueous hydrogen peroxide commercially available from Sigma-Aldrich) and/or an organic peroxide. Other examples of oxidizing agents include electron accepting compounds, nitric acid, sulfuric acid, hydrochloric acid, peroxydisulfuric acid, hydrochloric acid, and peroxymonosulfuric acid. Preferably, the oxidizing agent is present in a concentration ranging from approximately (i.e., +/−10 percent) 0.5 percent by weight to approximately (i.e., +/−10 percent) 25.0 percent by weight, and more preferably from approximately (i.e., +/−10 percent) 0.5 percent by weight to approximately (i.e., +/−10 percent) 5.0 percent by weight.

For purposes of the present disclosure, the stabilizing system comprises a first stabilizing agent and a second stabilizing agent. In a preferred implementation of the present invention, the first stabilizing agent comprises a sterically hindered phenolic antioxidant (e.g., pentaerythritol tetrakis(3-(3,5-di-tert-butyl-4-hydroxyphenyl)-propionate; "PTP") commercially available from Sigma-Aldrich, BASF, etcetera), and the second stabilizing agent comprises an organic ester (e.g., octyl gallate commercially available from Sigma-Aldrich).

In another preferred implementation of the present invention, the first stabilizing agent is a compound represented by the structure of formula (I):

wherein $R_1$-$R_3$ are each independently selected from the group consisting of H, OH, and an alkyl, aryl, alkoxy, alkanoyl, aroyl, alkenyl, and/or cyano group containing 1 to 25 carbon atom(s) with the proviso that at least one of $R_1$-$R_3$ is OH; wherein m ranges from 1 to 20; and wherein n ranges from 1 to 20.

In yet another preferred implementation of the present invention, the first stabilizing agent is a compound represented by the structure of formula (II):

wherein $R_1$-$R_3$ are each independently selected from the group consisting of H, OH, and an alkyl, aryl, alkoxy, alkanoyl, aroyl, alkenyl, and/or cyano group containing 1 to 25 carbon atom(s) with the proviso that at least one of $R_1$-$R_3$ is OH; and wherein m ranges from 1 to 5.

In one aspect of the present invention, the first stabilizing agent is a compound represented by the structure of formula (III):

In a preferred embodiment of the present invention, the second stabilizing agent is a compound represented by the structure of formula (IV):

wherein $R_1$-$R_3$ are each independently selected from the group consisting of H, OH, and an alkyl, aryl, alkoxy, alkanoyl, aroyl, alkenyl, and/or cyano group containing 1 to 25 carbon atom(s) with the proviso that at least one of $R_1$-$R_3$ is OH; and wherein m ranges from 1 to 20.

In another preferred embodiment of the present invention, the second stabilizing agent is a compound represented by the structure of formula (V):

wherein m ranges from 1 to 20.

In yet another preferred embodiment of the present invention, the second stabilizing agent is a compound represented by the structure of formula (VI):

Preferably, the stabilizing system is present in a concentration ranging from approximately (i.e., +/−10 percent) 0.001 percent by weight to approximately (i.e., +/−10 percent) 5.00 percent by weight, and more preferably from approximately (i.e., +/−10 percent) 0.01 percent by weight to approximately (i.e., +/−10 percent) 2.00 percent by weight.

For purposes of the present disclosure, the cleaning solution comprises one or more surfactants, such as, but not limited to, a non-ionic surfactant, an anionic surfactant, a cationic surfactant, a zwitterionic surfactant, and combinations thereof.

Non-limiting examples of preferred anionic surfactants include taurates; isethionates; alkyl and alkyl ether sulfates; succinamates; alkyl sulfonates, alkylaryl sulfonates; olefin sulfonates; alkoxy alkane sulfonates; sodium and potassium salts of fatty acids derived from natural plant or animal sources or synthetically prepared; sodium, potassium, ammonium, and alkylated ammonium salts of alkylated and acylated amino acids and peptides; alkylated sulfoacetates; alkylated sulfosuccinates; acylglyceride sulfonates, alkoxyether sulfonates; phosphoric acid esters; phospholipids; and combinations thereof. Specific anionic surfactants contemplated for use include, but are by no means limited to, ammonium cocoyl isethionate, sodium cocoyl isethionate, sodium lauroyl isethionate, sodium stearoyl isethionate, sodium lauroyl sarcosinate, sodium cocoyl sarcosinate, sodium lauryl sarcosinate, disodium laureth sulfosuccinate, sodium lauryl sulfoacetate, sodium cocoyl glutamate, TEA-cocoyl glutamate, TEA cocoyl alaninate, sodium cocoyl taurate, potassium cetyl phosphate.

Non-limiting examples of preferred cationic surfactants include alkylated quaternary ammonium salts $R_4NX$; alkylated amino-amides $(RCONH-(CH_2)_n)NR_3X$; alkylimidazolines; alkoxylated amines; and combinations thereof. Specific examples of anionic surfactants contemplated for use include, but are by no means limited to, cetyl ammonium chloride, cetyl ammonium bromide, lauryl ammonium chloride, lauryl ammonium bromide, stearyl ammonium chloride, stearyl ammonium bromide, cetyl dimethyl ammonium chloride, cetyl dimethyl ammonium bromide, lauryl dimethyl ammonium chloride, lauryl dimethyl ammonium bromide, stearyl dimethyl ammonium chloride, stearyl dimethyl ammonium bromide, cetyl trimethyl ammonium chloride, cetyl trimethyl ammonium bromide, lauryl trimethyl ammonium chloride, lauryl trimethyl ammonium bromide, stearyl trimethyl ammonium chloride, stearyl trimethyl ammonium bromide, lauryl dimethyl ammonium chloride, stearyl dimethyl cetyl ditallow dimethyl ammonium chloride, dicetyl ammonium chloride, dilauryl ammonium chloride, dilauryl ammonium bromide, distearyl ammonium chloride, distearyl ammonium bromide, dicetyl methyl ammonium chloride, dicetyl methyl ammonium bromide, dilauryl methyl ammonium chloride, distearyl methyl ammonium chloride, distearyl methyl ammonium bromide, ditallow dimethyl ammonium chloride, ditallow dimethyl ammonium sulfate, di(hydrogenated tallow) dimethyl ammonium chloride, di(hydrogenated tallow) dimethyl ammonium acetate, ditallow dipropyl ammonium phosphate, ditallow dimethyl ammonium nitrate, di(coconutalkyl)dimethyl ammonium chloride, di(coconutalkyl)dimethyl ammonium bromide, tallow ammonium chloride, coconut ammonium chloride, stearamidopropyl PG-imonium chloride phosphate, stearamidopropyl ethyldimonium ethosulfate, stearimidopropyldimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, ditallowyl oxyethyl dimethyl ammonium chloride, behenamidopropyl PG dimonium chloride, dilauryl dimethyl ammonium chloride, distearly dimethyl ammonium chloride, dimyristyl dimethyl ammonium chloride, dipalmityl dimethyl ammonium chloride, distearyl dimethyl ammonium chloride, stearamidoproyl PG-dimonium chloride phosphate, stearamidopropyl ethyldiammonium ethosulfate, stearamidopropyl dimethyl (myristyl acetate) ammonium chloride, stearimidopropyl diemthyl cetaryl ammonium tosylate, stearamido propyl dimethyl ammonium chloride, stearamidopropyl dimethyl ammonium lactate.

Non-limiting examples of preferred non-ionic surfactants include alcohols, alkanolamides, amine oxides, esters (including glycerides, ethoxylated glycerides, polyglyceryl esters, sorbitan esters, carbohydrate esters, ethoxylated carboxylic acids, phosphoric acid triesters), ethers (including ethoxylated alcohols, alkyl glucosides, ethoxylated polypropylene oxide ethers, alkylated polyethylene oxides, alkylated polypropylene oxides, alkylated PEG/PPO copolymers), silicone copolyols. Specific examples of non-ionic surfactants contemplated for use include, but are by no means limited to, cetearyl alcohol, ceteareth-20, nonoxynol-9, C12-15 pareth-9, POE(4) lauryl ether, cocamide DEA, glycol distearate, glyceryl stearate, PEG-100 stearate, sorbitan stearate, PEG-8 laurate, polyglyceryl-10 trilaurate, lauryl glucoside, octylphenoxy-polyethoxyethanol, PEG-4 laurate, polyglyceryl diisostearate, polysorbate-60, PEG-200 isostearyl palmitate, sorbitan monooleate, polysorbate-80.

Non-limiting examples of preferred zwitterionic or amphoteric surfactants include betaines; sultaines; hydroxysultaines, amido betaines, amidosulfo betaines; and combinations thereof. Specific examples of amphoteric surfactants contemplated for use include, but are by no means limited to, cocoamidopropyl sultaine, cocoamidopropyl hydroxyl sultaine, cocoamidopropylbetaine, coco dimethyl carboxymethyl betaine, lauryl dimethyl carboxymethyl betaine, lauryl dimethyl alphacarboxyethyl betaine, cetyl dimethyl carboxymethyl betaine, cetyl dimethyl betaine, lauryl (2-bishydroxy) carboxymethyl betaine, stearyl bis-(2-hydroxyethyl) carboxymethyl betaine, oelyl dimethyl gamma-carboxypropyl betaine, lauryl bis-(2-hydroxypropyl)alpha carboxymethyl betaine, coco dimethyl sulfopropyl betaine, stearyl dimethyl sulfopropyl betaine, lauryl dimethyl sulfoethyl betaine, lauryl bis(2-hydroxyethyl) sulfopropyl betaine, oleyl betaine, cocamidopropyl betaine.

Preferably, surfactant(s) are present in a concentration ranging from approximately (i.e., +/−10 percent) 0.05 percent by weight to approximately (i.e., +/−10 percent) 25 percent by weight, and more preferably from approximately (i.e., +/−10 percent) 0.5 percent by weight to approximately (i.e., +/−10 percent) 15 percent by weight.

In one preferred embodiment of the present invention, the cleaning solutions/formulations may comprise one or more adjunct agents including, but not limited to, herbal additives, anti-oxidants, buffers, scents, fragrances, colorants, and/or stabilizers.

Preferably, adjunct agent(s) are present in a concentration ranging from approximately (i.e., +/−10 percent) 0.05 percent by weight to approximately (i.e., +/−10 percent) 25 percent by weight, and more preferably from approximately (i.e., +/−10 percent) 0.5 percent by weight to approximately (i.e., +/−10 percent) 5 percent by weight.

It will be understood that other weights, weight ratios, and ranges are obtainable from the Examples provided hereinbelow.

Provided below are non-limiting examples of cleaning solution formulations in accordance with the present invention, wherein the stabilizing system stabilizes both the hydrogen peroxide and the fragrance and/or color components within those formulations.

Example 1

| Ingredient Name | Phase | Amount (% by Wt.) |
| --- | --- | --- |
| Water | A | q.s. to 100 |
| Hydrogen peroxide | A | 4.00 |
| PTP | A | 0.04 |
| Octyl gallate | A | 0.02 |

Example 2

| Ingredient Name | Phase | Amount (% by Wt.) |
| --- | --- | --- |
| Water | A | q.s. to 100 |
| Hydrogen peroxide | A | 8.00 |
| PTP | A | 0.08 |
| Octyl gallate | A | 0.02 |

Example 3

| Ingredient Name | Phase | Amount (% by Wt.) |
| --- | --- | --- |
| Water | A | q.s. to 100 |
| Hydrogen peroxide | A | 4.00 |
| PTP | A | 0.03-0.06 |
| Octyl gallate | A | 0.02-0.04 |
| Orange Oil | A | 1.78 |
| Surfactants | A | 4.34 |

Example 4

| Ingredient Name | Phase | Amount (% by Wt.) |
| --- | --- | --- |
| Water | A | q.s. to 100 |
| Hydrogen peroxide | A | 8.00 |
| PTP | A | 0.05-0.08 |
| Octyl gallate | A | 0.03-0.06 |
| Orange Oil | A | 3.54 |
| Surfactants | A | 8.64 |

Example 5

| Ingredient Name | Phase | Amount (% by Wt.) |
| --- | --- | --- |
| Water | A | q.s. to 100 |
| Hydrogen peroxide | A | 4.00-8.00 |
| PTP | A | 0.05-0.08 |
| Octyl gallate | A | 0.03-0.06 |
| Surfactants | A | 4.00-10.00 |

Example 6

| Ingredient Name | Phase | Amount (% by Wt.) |
| --- | --- | --- |
| Water | A | q.s. to 100 |
| Hydrogen peroxide | A | 4.00-8.00 |
| PTP | A | 0.05-0.08 |
| Octyl gallate | A | 0.03-0.06 |
| Orange Oil | A | 2.50-6.50 |
| Surfactants | A | 4.00-10.00 |

Procedure:

1. PHASE A in main vessel, add Phase A ingredients one at a time and mix until completely dissolved and uniform. A Silverson L5M-A homogenizer at 3,750 RPM expedites formation of the stable, homogenous dispersion/emulsion.

It will be further understood that any reference to compounds disclosed herein includes salts and/or solvates of the same.

The foregoing description merely explains and illustrates the invention and the invention is not limited thereto except insofar as the appended claims are so limited, as those skilled in the art who have the disclosure before them will be able to make modifications without departing from the scope of the invention.

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms "comprising," "including," "containing," etcetera shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etcetera. As a non-limiting example, each range discussed herein can be readily broken down into a lower third, middle third and upper third, etcetera. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims.

What is claimed and desired to be secured by Letters Patent of the United States is:

1. A cleaning solution, comprising:
   a solvent;
   an oxidizing agent, wherein the oxidizing agent comprises a peroxide;
   a stabilizing system, wherein the stabilizing system comprises a first stabilizing agent comprising a sterically hindered phenolic antioxidant, and a second stabilizing agent comprising an organic ester;
   a surfactant;
   an optional colorant; and
   an optional fragrance.

2. The cleaning solution according to claim 1, wherein the solvent comprises water.

3. The cleaning solution according to claim 1, wherein the peroxide is selected from the group consisting of an inorganic peroxide and an organic peroxide.

4. The cleaning solution according to claim 1, wherein the peroxide comprises hydrogen peroxide.

5. The cleaning solution according to claim 1, wherein the first stabilizing agent is a compound represented by the structure of formula (I):

wherein $R_1$-$R_3$ are each independently selected from the group consisting of H, OH, and an alkyl, aryl, alkoxy, alkanoyl, aroyl, alkenyl, and/or cyano group containing 1 to 25 carbon atom(s) with the proviso that at least one of $R_1$-$R_3$ is OH;

wherein m ranges from 1 to 20; and wherein n ranges from 1 to 20.

6. The cleaning solution according to claim 1, wherein the first stabilizing agent is a compound represented by the structure of formula (II):

wherein m ranges from 1 to 5.

7. The cleaning solution according to claim 1, wherein the first stabilizing agent is a compound represented by the structure of formula (III):

8. The cleaning solution according to claim 1, wherein the second stabilizing agent is a compound represented by the structure of formula (IV):

wherein $R_1$-$R_3$ are each independently selected from the group consisting of H, OH, and an alkyl, aryl, alkoxy, alkanoyl, aroyl, alkenyl, and/or cyano group containing 1 to 25 carbon atom(s) with the proviso that at least one of $R_1$-$R_3$ is OH; and wherein m ranges from 1 to 20.

9. The cleaning solution according to claim 1, wherein the second stabilizing agent is a compound represented by the structure of formula (V):

(V)

wherein m ranges from 1 to 20.

10. The cleaning solution according to claim 1, wherein the second stabilizing agent is a compound represented by the structure of formula (VI):

(VI)

11. The cleaning solution according to claim 1, wherein the surfactant comprises a non-ionic surfactant, an anionic surfactant, a cationic surfactant, a zwitterionic surfactant, and combinations thereof.

12. The cleaning solution according to claim 1, wherein the optional colorant is D-limonene, and/or orange oil.

13. The cleaning solution according to claim 1, wherein the optional fragrance is D-limonene, and/or orange oil.

14. A cleaning solution, consisting of:
a solvent, wherein the solvent is water;
an oxidizing agent, wherein the oxidizing agent is hydrogen peroxide;
a stabilizing system, wherein the stabilizing system consists of a first stabilizing agent and a second stabilizing agent, wherein the first stabilizing agent is a sterically hindered phenolic antioxidant and the second stabilizing agent is an organic ester, and wherein the weight ratio of the first stabilizing agent to hydrogen peroxide is approximately 1:50 to 1:160, and the weight ratio of the second stabilizing agent to hydrogen peroxide is approximately 1:67 to 1:267;
a surfactant, wherein the surfactant is a non-ionic surfactant, an anionic surfactant, a cationic surfactant, a zwitterionic surfactant, and combinations thereof; and
a colorant/fragrance, wherein the colorant/fragrance is orange oil.

15. A cleaning solution, consisting of:
from approximately 75% to approximately 98% by weight a solvent, wherein the solvent is water;
from approximately 0.5% to approximately 5.0% by weight an oxidizing agent, wherein the oxidizing agent is hydrogen peroxide;
from approximately 0.01% to approximately 2.0% by weight a stabilizing system, wherein the stabilizing system is pentaerythritol tetrakis(3-(3,5-di-tert-butyl-4-hydroxyphenyl) propionate) and octyl gallate, and wherein the weight ratio of pentaerythritol tetrakis(3-(3,5-di-tert-butyl-4-hydroxyphenyl) propionate) to hydrogen peroxide is approximately 1:50 to 1:160, and the weight ratio of octyl gallate to hydrogen peroxide is approximately 1:67 to 1:267;
from approximately 0.5% to approximately 15.00% by weight a surfactant;
from approximately 0.5% to approximately 5.00% by weight a colorant/fragrance; and
wherein any remainder consists of one or more adjunct agents.

16. The cleaning solution according to claim 1, wherein the weight ratio of the first stabilizing agent to hydrogen peroxide is approximately 1:50 to 1:160, and the weight ratio of the second stabilizing agent to hydrogen peroxide is approximately 1:67 to 1:267.

* * * * *